US011065269B1

(12) United States Patent
Shepherd

(10) Patent No.: US 11,065,269 B1
(45) Date of Patent: Jul. 20, 2021

(54) METHOD OF USING ASTAXANTHIN FOR THE TREATMENT OF DISEASES, AND MORE PARTICULARLY, THE TREATMENT OF CANCER

(71) Applicant: Samuel L. Shepherd, Cypress, TX (US)

(72) Inventor: Samuel L. Shepherd, Cypress, TX (US)

( * ) Notice: Subject to any disclaimer, the term of this patent is extended or adjusted under 35 U.S.C. 154(b) by 0 days.

(21) Appl. No.: 16/683,996

(22) Filed: Nov. 14, 2019

Related U.S. Application Data

(60) Provisional application No. 62/767,648, filed on Nov. 15, 2018.

(51) Int. Cl.
| | |
|---|---|
| *A61K 31/7034* | (2006.01) |
| *A61K 9/00* | (2006.01) |
| *A61K 47/44* | (2017.01) |
| *A61K 47/46* | (2006.01) |
| *A23L 33/105* | (2016.01) |

(52) U.S. Cl.
CPC ........ *A61K 31/7034* (2013.01); *A61K 9/0014* (2013.01); *A61K 9/0053* (2013.01); *A61K 47/44* (2013.01); *A61K 47/46* (2013.01); *A23L 33/105* (2016.08)

(58) Field of Classification Search
CPC .............. A61K 31/7034; A61K 9/0014; A61K 9/0053; A61K 47/46; A61K 47/44; A23L 33/105
See application file for complete search history.

(56) References Cited

U.S. PATENT DOCUMENTS

| | | | |
|---|---|---|---|
| 6,022,701 | A | 2/2000 | Boussiba et al. |
| 6,262,316 | B1 * | 7/2001 | Wadstrom ................ A61P 1/02 568/834 |
| 7,063,957 | B2 | 6/2006 | Chen |
| 2004/0077036 | A1 | 4/2004 | Thomas et al. |
| 2005/0124032 | A1 | 6/2005 | De La Fuente Moreno et al. |
| 2010/0285557 | A1 | 11/2010 | Martin et al. |

OTHER PUBLICATIONS

Matsushita et al., Fisheries Science, 2000, 66, p. 980-985. (Year: 2000).*
Yokoyama et al., Journal of Natural Products, 1995, 58(12), p. 1929-1933. (Year: 1995).*
Ambati et al., Mar. Drugs, 2014, 12, p. 128-152. (Year: 2014).*
Bornaghi et al., Tetrahedron Letters, 2005, 46, p. 3485-3488. (Year: 2005).*
CEM Discover Operation Manual, CEM Corporation, 2006, Rev 6, 59 pages. (Year: 2006).*
Hama et al., J. Pharm. Sci., 2012, 101, p. 2909-2916. (Year: 2012).*

* cited by examiner

*Primary Examiner* — Jonathan S Lau
(74) *Attorney, Agent, or Firm* — Egbert, McDaniel & Swartz, PLLC

(57) ABSTRACT

A method of treating a subject afflicted with cancer, arthritis, diabetes, lupus, fibromyalgia or dementia includes administering a therapeutic amount of a glucosidic astaxanthin to the subject in need of such treatment. The glucosidic astaxanthin is prepared by reacting astaxanthin with a monosaccharide at a temperature so as to produce the glucosidic astaxanthin. The therapeutic amount is not is greater than 0.1 milligrams per kilogram of body weight per day. The glucosidic astaxanthin can be added to a carrier material, such as an edible material, a pill, or oil.

10 Claims, No Drawings

US 11,065,269 B1

METHOD OF USING ASTAXANTHIN FOR THE TREATMENT OF DISEASES, AND MORE PARTICULARLY, THE TREATMENT OF CANCER

RELATED U.S. APPLICATIONS

The present application claims priority from U.S. Provisional Patent Application Ser. No. 62/767,648, filed on Nov. 15, 2018, and entitled "Method of Using Astaxanthin for the Treatment of Diseases, and More Particularly, the Treatment of Cancer".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to treating disease. More particularly, the present invention relates to methods for the treatment of cancer. In particular, the present invention relates to the use of astaxanthin for the treatment of disease.

2. Description of Related Art Including Information Disclosed Under 37 CFR 1.97 and 37 CFR 1.98

Astaxanthin is a xanthophyll of great interest in animal nutrition and human health. The market prospect in the nutraceuticals industries for this health-protective molecule is very promising. There is a current multi-billion dollar demand for astaxanthin which increases at over 28% per annum.

Astaxanthin is currently synthesized by several bacteria, algae and plants from beta-carotene by the sequential action of two enzymes: (1) a beta-carotene enzyme, 3,3'-hydroxylase that introduces an hydroxyl group at the 3 (and 3') positions of each of the two beta-ionone rings of beta-carotene, and a beta-carotene ketolase that introduces keto groups at carbons 4 and 4' of the ß-ionone rings. Astaxanthin is also produced by the yeast-like basidiomycete *Xanthophyllomyces dendrorhous*.

Carotenoids are an important group of naturally-occurring pigments with uses ranging from colorants, feed supplements and nutraceuticals. Carotenoids are also used for medical, cosmetic and biotechnological purposes. Although more than 600 carotenoids have been described from carotenogenic microorganisms, only beta-carotene, lycopene and astaxanthin are commercially produced by microbial fermentation. These three compounds have various biological functions such as species-specific coloration, light-harvesting, photo-protection, antioxidant, and hormone precursor. Dietary carotenoids have beneficial effects which delay the onset of many diseases such as arteriosclerosis, cataracts, age-related macular degeneration, multiple sclerosis, cardio-vascular diseases, and some kinds of cancer. For these reasons, the demand and market of carotenoids have grown drastically.

Astaxanthin is a lipid-soluble keto-carotenoids having a deep red color. The high electrode negativity of astaxanthin is a direct result of its hydroxyl and ketone functional groups (carboxylic acid groups) established on both ends of a carbon chain of alternating double bonds. This "dumbbell" shaped molecule has a central region of electrons that can be donated or adsorbed to reduce a reactive oxidizing molecule, such as PD-1, PD-L1 and PD-L2. Astaxanthin, unlike several carotenes and one other known carotenoid, is not converted to vitamin A (retinol) in the human body. Like other carotenoids, astaxanthin has self-limited absorption orally and low toxicity. No toxic side effects have been observed.

Astaxanthin, as a free radical scavenger/antioxidant, is 400 times more reactive as an antioxidant than betacarotene. Astaxanthin is not only the world's strongest natural antioxidant, astaxanthin is also a safe and natural anti-inflammatory. Astaxanthin is incredibly potent and well-rounded in its antioxidant activity. As an example, in an antioxidant test identified as "singlet oxygen quenching", astaxanthin has been shown to be 550 times stronger than vitamin E, 800 times stronger than CoQ10 and 6000 times stronger than vitamin C.

In the past, various patents and patent publications have been directed to the production of astaxanthin. For example, U.S. Patent Publication No. 2010/0285557, published on Nov. 11, 2010 to Martin et al., pertains to a method for the efficient production of carotenoids. In particular, this invention is directed to a method for producing carotenoid and carotenoid-containing cells, especially astaxanthin and astaxanthin-containing cells, by generating mutant microorganisms belonging to the photoautotrophic algae of the class chlorophyceae and culturing the same.

U.S. Pat. No. 7,063,957, issued on Jun. 20, 2006 to F. Chen, discloses a methods for producing ketocarotenoid astaxanthin by the green microalga *Chlorella* zofingiensis in dark-heterotrophic cultures so as to provide excellent growth and high-yield astaxanthin production on glucose-supplemented media in the dark.

U.S. Patent Publication No. 2005/0124032, published on Jun. 9, 2005 to De La Fuente Moreno et al., teaches a method of producing of astaxanthin by fermenting selected strains of *Xanthophyllomyces dendrorhous*. These strains are selected based on: (i) resistance to inhibitors of steroid synthesis, to inhibitors of respiration and to compounds that induce the formation of free radicals; (ii) color intensity of the colony and production of carotenoids on solid medium; (iii) production of astaxanthin in darkness; (iv) production of astaxanthin in conditions with a raised temperature; and (v) production of astaxanthin with carbon sources other than glucose.

U.S. Patent Publication No. 2004/0077036, published on Apr. 22, 2004 to Thomas et al., provides a process to produce astaxanthin from *haematococcus* biomass. In particular, a modified nutrient medium containing four nitrogen sources is used for culturing the algae. Green motile cells produced are converted into dormant red cysts which are chilled and stressed for vigorous multiplication. Nutrients are added gradually and the initial germination is carried out without carbon dioxide sparging. The dilution stage is also effected in the absence of carbon dioxide. The stressed red cysts are regerminated and the cycle repeated to produce a biomass enriched with astaxanthin.

U.S. Pat. No. 6,022,701, issued on Feb. 8, 2000 to Boussiba et al., discloses a procedure for large-scale production of astaxanthin from *haematococcus*. In this process the *haematococcus* cells are cultivated under conditions suitable for optimal vegetative growth of such cells and the cells are collected and cultivated under conditions suitable for optimal induction and accumulation of astaxanthin in the cells. The cells are inoculating into a growth solution containing essentially a carbon source and growing the cells at a temperature of below 35° C.

It is an object of the present invention to provide a method for treatment of disease that reinstates membrane electrical potential across the cell membrane to manipulate adsorption of nutrients, ions, fatty acids and sterols.

It is another object of the present invention to provide a method for the treatment of disease that reduces intracellular sodium concentrations.

It is another object of the present invention to provide a method for the treatment of disease which increases intracellular delivery of magnesium, potassium and calcium.

It is another object of the present invention to provide a method for treating disease which removes excess reactive oxygen species, and eliminates further DNA mutation from the external surface of cancer cells.

It is another object of the present invention to provide a method for the treatment of disease which inhibits PD-L1/PD-L2 deactivation of T cells.

It is another object of the present invention to provide a method for the treatment of disease which corrects intracellular, extracellular and membrane measures of the abnormal electrical properties of cancer cells.

It is another object of the present invention provide a method for the treatment of disease which results in the destruction of the cancer cells.

It is still a further object the present invention to provide a method for the treatment of disease which reduces intracellular water accumulation.

These and other objects and advantages of the present invention will become apparent from a reading of the attached specification and appended claims.

BRIEF SUMMARY OF THE INVENTION

The present invention is a method of treating the subject afflicted with cancer, arthritis, diabetes, lupus, fibromyalgia or dementia. This method includes the step of administering a therapeutic amount of a glucosidic astaxanthin to the subject in need of such treatment. The glucosidic astaxanthin has the following chemical structure:

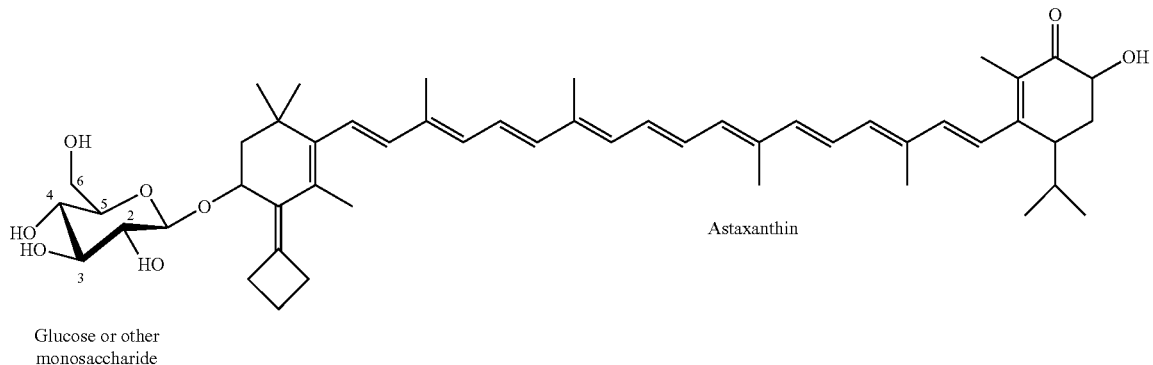

Glucose or other monosaccharide

In the present invention, the glucosidic astaxanthin can be added to a carrier material. This carrier material can be edible, such as chocolate or a pill. Alternatively, the carrier material can be an oil.

The therapeutic amount is greater than 0.1 milligrams per kilogram of body weight per day. The therapeutic amount is, preferably, between 24 and 40 milligrams per kilogram of body weight per day. In those cases where the subject is afflicted with cancer, arthritis or diabetes, the therapeutic amount is 1 milligram per kilogram of body weight per day.

In one embodiment, the step of administering is by orally consuming the glucosidic astaxanthin. Alternatively, the step of administering can be by dermally applying the glucosidic astaxanthin onto an area of the skin of a subject afflicted with skin cancer.

In the method of the present invention, the glucosidic astaxanthin is prepared prior to the step of administering. In particular, the astaxanthin is reacted with a monosaccharide at a temperature so as to produce the glucosidic astaxanthin. In the preferred embodiment of the present invention, the astaxanthin is reacted with the monosaccharide at a microwave frequency of between 1 and 100 GHz for at least one second and no more than twenty-five seconds.

The present invention is also a method of treating a subject afflicted with a disease. This method includes the steps of: (1) preparing a composition containing astaxanthin; and (2) administering a therapeutic amount of the astaxanthin-containing composition to the subject having to the disease. In this method, the astaxanthin-containing composition is glucosidic astaxanthin. The step of preparing comprises reacting the astaxanthin with a monosaccharide at a temperature so as to produce the glucosidic astaxanthin. The disease is selected from the group consisting of cancer, arthritis, diabetes, lupus, fibromyalgia and dementia. The glucosidic astaxanthin has the following formula:

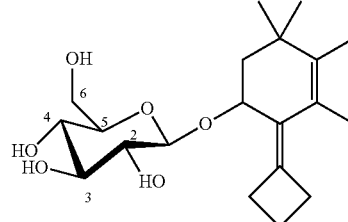

Glucose or other monosaccharide

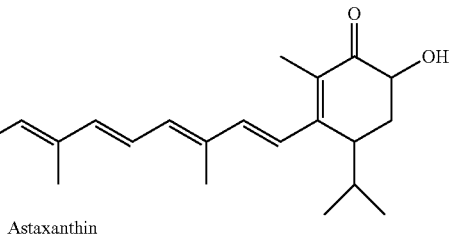

Astaxanthin

The step of administering can include adding the astaxanthin-containing composition to a carrier material.

The method for treating disease the present invention provides improved cell membrane electrical potential and membrane capacitance, along with PD-L1 interference and inhibition. This results from the therapeutic amount of astaxanthin being four milligrams per kilogram body weight. This has been shown to convert anaerobic mitochondrial production of ATP to aerobic mitochondrial production. This method reduces hydrogen and cation concentration and increases cellular pH. This method stabilizes sodium and potassium ion concentration gradients. The method of the present invention alters cell membrane permeability of sodium and potassium ions. The method of the present invention returns cancer cell electrical potential to normal cell potential. The present invention provides reduced inflammation response resulting from large sodium intracellular concentration. The present invention maximizes production, inhibition and expression of proteins and other macro molecules such as PD-1, PD-L1, PD-L2 sodium and potassium channel proteins and sodium/potassium pump proteins. The present invention also improves the absorption of certain nutrients, including essential fatty acids, phospholipids, sterols and nutrients, along with mineral transporter ions, such as sodium, potassium, magnesium and calcium. This helps normalize intracellular mineral concentration gradients in diseased cells. The combination of cell membrane repair, inactivation of PD-L1 and PD-L2, increased cellular pH, correction of deficiencies of intracellular mineral concentrations and correction of excessive intracellular levels of sodium results in the overall improvement of cell membrane capacitance and electrical polarization.

In experiments conducted with the present invention, it is been shown that increasing astaxanthin levels in the diet can be used as a pre-cancer, cancer and anti-inflammatory prophylactic at levels up to 400 mg per day. No discernible side effects of astaxanthin have been observed at those levels up to 400 mg per day. There was some decolorization of feces resulting from unabsorbed astaxanthin. Anti-inflammatory and pain reduction associated with arthritis were noted within four weeks of treatment of greater than 50 mg per day. No side effects or skin color changes were observed. High intracellular sodium and low potassium levels were observed in cancerous cells.

This foregoing Section is intended to describe, with particularity, the preferred embodiments of the present invention. It is understood that modifications to these preferred embodiments can be made within the scope of the appended claims. As such, this Section should not to be construed, in any way, as limiting of the broad scope of the present invention. The present invention should only be limited by the following claims and their legal equivalents.

DETAILED DESCRIPTION OF THE INVENTION

The present invention is a technique for administering astaxanthin to a patient afflicted with a disease. In particular, disease can be cancer, arthritis, diabetes, lupus, fibromyalgia or dementia. In particular, so as to achieve the benefits of the present invention, a therapeutic amount of a glucosidic astaxanthin is administered to the subject in need of such treatment. This glucosidic astaxanthin will have the following chemical structure:

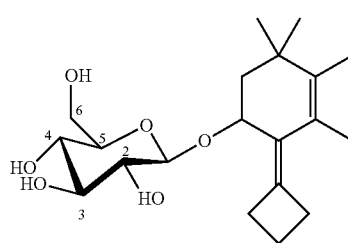

Glucose or other monosaccharide

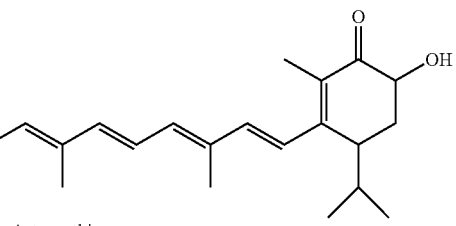

Astaxanthin

In order to administer the glucosidic astaxanthin, the glucosidic astaxanthin is added to a carrier material. Typically, this carrier material can be in the nature of a pill, an edible substance or an oil. In particular, the glucosidic astaxanthin can be added to a carrier material, such as chocolate. If the glucosidic astaxanthin is to be administered dermally, then it can be added to an oil.

In order to achieve the advantages of the present invention, the therapeutic amount of the glucosidic astaxanthin should be greater than 0.1 milligrams per kilogram of body weight per day. Preferably, the therapeutic amount is between 24 and 400 milligrams per kilogram of body weight per day. In those circumstances where the subject has cancer, arthritis or diabetes, the therapeutic amount is between one milligram per kilogram of body weight per day.

The glucosidic astaxanthin can be administered by orally consuming the glucosidic astaxanthin or by dermally applying the glucosidic astaxanthin. Under those circumstances where the glucosidic astaxanthin is dermally applied, it would be applied to an area of the skin of the subject in those circumstances where the subject is afflicted with a skin cancer. The glucosidic astaxanthin can be applied directly onto the lesions caused by melanoma, basal cell carcinomas or other inflammatory lesions.

The glucosidic astaxanthin is prepared prior to the step of administering. In particular, the astaxanthin is reacted with a monosaccharide at a temperature so as to produce the glucosidic astaxanthin. In particular, the astaxanthin is reacted with the monosaccharide at a microwave frequency of between 1 and 100 GHz for at least one second and no more than twenty-five seconds.

The technology in which the astaxanthin is effective in treating these particular diseases is described hereinafter.

Cell membranes are composed of bilayer of highly mobile lipid molecules that electrically act as an insulator or (i.e. a dielectric). The insulating properties of cell membrane lipids also act to restrict the movement of charged ions and electrons across the membrane except through specialized protein "gates" known as ion channels. Since the cell membrane is selectively permeable to sodium and potassium ions, a different concentration of these and other charged mineral ions will build up on either side of the membrane. The different concentrations and electron negativities of these charged molecules cause the outer membrane surface to have a relatively higher positive charge than the inner membrane surface. This results in creating an electrical potential across the membrane.

All cells have an imbalance in electrical charge between the inside of the cell and the outside of the cell. The difference is known as the membrane potential. This membrane electrical potential is created by the difference in the concentration of ions inside and outside of the cell. This electrical potential creates an electrochemical force across the cell membrane. The electrochemical force is across the membrane regulate chemical exchange across the cell. The cell membrane potential helps control cell membrane transport of a variety of nutrients and is essential in the metabolism and conversion of ADP into ATP.

All living cells have a membrane potential of −60 to −100 mV. The negative sign of the membrane potential indicates that the inside surface of the cell membrane is relatively more negative than the outside of the cell membrane. This is due to the differing electron negatives of potassium ions and organic proteins.

In a healthy normal cell, there are low concentrations of PD-L1/PD-L2 expression, higher concentrations of K+ ions, and negatively charged proteins on the inside surface of the cell membrane. Therefore, since a high concentration of positively-charged sodium ions are on the outside of the cell, the interior of the cell is slightly more negative than the exterior of the cell membrane. This creates an electrical potential across the cell membrane. This large electrical potential across the cell membrane has been measured up to −18 million to −23 million volts/meter in healthy cells and 0 to −16 million volts/meter in cancerous or damaged cells.

Healthy cells maintain a high concentration of potassium in a low concentration of sodium within the cell membrane. In cancer, there are changes in the cell membrane structure, changes in the membrane function, changes in the cell concentration of minerals, changes in cell membrane electrical potential, changes in the electrical connections within the cells and between the cells, and changes in cellular energy production. When the cells are injured or cancerous, or during hypoxia, more sodium leak channels exist and more leak potassium channels are present. The sodium/potassium pump is ineffective. The dielectric properties of the phospholipid membrane is compromised. When activated, water, hydrogen ions and excess sodium ions flow into the cells. Potassium, magnesium, calcium and zinc are lost from the interior of the cell and the cell membrane potential falls. This collapse in electrical potential will convert the metabolism of the cell from that of oxidative to a reductive metabolism and the cellular pH decreases from 7.35 to as low as 5.8. A reductive anaerobic/anabolic metabolism favors abnormal cancer cell growth in cellular inflammation, along with increased expression of PD-L1/PD-L2 into the cancerous cell membrane.

Cells have many discrete electrical zones. A cell contains four are electrified zones. A central zone contains negatively charged organic molecules and maintains a steady bulk negativity. An inner positive zone exists between the inner aspect of the cell membrane and the central negative zone. The inner positive zone is composed of a thin layer of freely mobile mineral cations, in particular, potassium and a small amount of calcium. The outer positive zone exists around the outer surface of the cell membrane and has a denser zone of mobile cations composed mostly of sodium, calcium and a small amount of potassium. Since the concentration of positive charges is larger on the outer surface of the cell membrane than the concentration of positive charges on the inner surface of the cell membrane, an electrical potential exists across the cell membrane. The existence of an outer electrically negative zone is composed of the glycocalyx. The outermost electrically negative zone is composed of negatively-charged sialic acid molecules that cap the tips of glycoproteins proteins and glycolipids that extend outward from the cell membrane in a manner similar to that of tree branches. The outermost negative zone is separated from the positive cell membrane by about twenty micrometers. It is this outermost calyx zone of steady negativity that makes each cell act as a negatively-charged body. Every cell creates a negatively-charged field around itself that influences any other charged body close to it. It is the negatively-charged sialic acid residues of the cell coat (i.e. glycocalyx) that gives each cell its zeta potential. Since the negatively-charged electrical field around the cells are created by sialic acid residues, any factor that increases or decreases the number of sialic acid residues will change the degree of surface negativity that a cell exhibits.

In cancer cells, the electrical activity is affected since the cancer cells are less efficient in their production of cellular

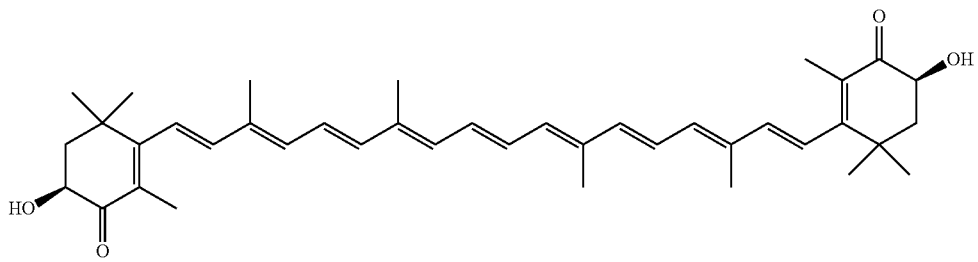 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O]

energy. Cancer cells metabolically favor anaerobic processes (i.e. without oxygen) over aerobic processes (i.e. with oxygen). Cancer cells have cell membranes that exhibit different electrochemical properties in a different distribution of electrical charges than normal tissues. Cancer cells have 100 to 1000 times the level of PD-L1 or PD-L2 expression at the cell membrane. Cancer cells also have different lipid and sterol contents than normal cells. Cancer cells have altered membrane composition and membrane permeability. This results in the movement of potassium, magnesium and calcium out of the cell and the accumulation of sodium and water into the cell. This causes tumor growth. These characteristics are all the result of an altered membrane electrical charge and increased levels of PD-L1 expression. It is these expressive proteins that appear to suppress T and B cell attack on cancer cells.

Astaxanthin, due to its high electronegativity and reactive carboxylic sites, inactivates the PD-L1 sites. This inactivation allows for immediate cancer cell lysis from the T cell attack. Due to the elevated level of expressed PD-L1 sites relative to normal cells, normal cells remain unaffected.

These cancer cell characteristics can be modified using carotenoid-type molecules that increases the pH from less than 7.0 to 7.2-7.4. The use of the carotenoid-type molecules eliminates the effects of PD-L1 and reduces the anaerobic metabolism of cancer cells. The most effective carotenoid is astaxanthin. Astaxanthin is beneficial in the treatment of the of diseases, such as cancer, due to its extreme effect on the electrical charge exhibited by the PD-L1 on the cell membrane and due to the high electronegativity of astaxanthin. Sialic acid residues from cancer cells are removed or reduced due to the astaxanthin/sialic acid reactions without any negative side effects to the normal cells. This causes the cancer to lose its metabolic functions. The elimination of the electrical charge on the PD-L1 protein and the loss of metabolic function results in apoptosis (i.e. cell death) and cell lysis resulting from macrophage and T and B cell-specific attack on the cancer cell. The astaxanthin, being electrically negative, preferentially adsorbs or neutralizes the cations of hydrogen and sodium inside the cell and increases the concentration of sodium on the exterior of the cell membrane. This returns the cell to a more favorable electrical potential which favors apoptosis of the cancer cell.

This makes the cancer cell more vulnerable to macrophage attack due to its altered state from anaerobic to aerobic. The reestablishment of the electrical potential across the cancer cell is achieved by using the high electronegativity of astaxanthin. The astaxanthin increases the polarization of the charge of the cell and thereby reduces the electrical abnormalities associated with the cancer cell.

The chemical structure of astaxanthin is illustrated hereinbelow:

As can be seen, the ends of the molecule are comprised of OH— and C═O (hydroxide/ketone) functional groups connected by a highly conjugated double-bonded carbon chain. This creates a reactive and electronic negatively-charged molecule. As such, it is capable of donating electrons and hydrogen bonding. The connecting structure of the lipid soluble molecule is essentially the same length as the width of the phospholipid cellular membrane, thereby residing within the structure of the cellular membrane.

The astaxanthin molecule, with its highly negative charge, attracts Na+ ions and inactivates PD-L1 and PD-L2 ligands. This configuration creates a polarization of the cancer cell, thereby increasing the electrical potential across the cell membrane. This increase in electrical potential causes sodium ions to accumulate on the exterior of the cell membrane, reduces the sodium concentration on the inside of the cell, and inhibits the functionality of the PD pathway. This returns the cell to normal cell function, decreases intracellular water content, and inhibits the T cell inactivation resulting in cell volume reduction and T cell attack on the cancerous cell.

The blocking and inhibition of PD-L1 by astaxanthin is shown chemically hereinbelow:

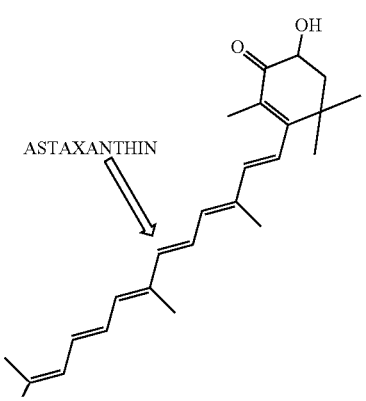

-continued

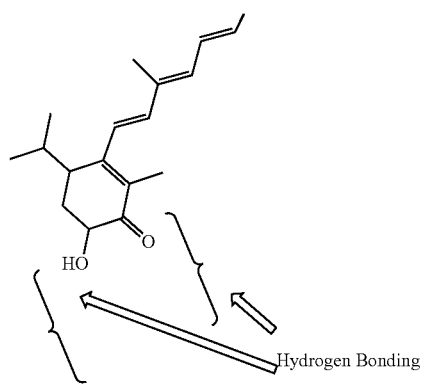

As can be seen by the above illustration, the tumor cell expressed PD-L1 combines with the PD-1 site of the T cell. This inactivates the T cell. astaxanthin inhibits the PD-L1 site through carboxylic acid reaction with the functional side of astaxanthin. By the following illustration, this reaction stops the binding of PD-1 to PD-L1.

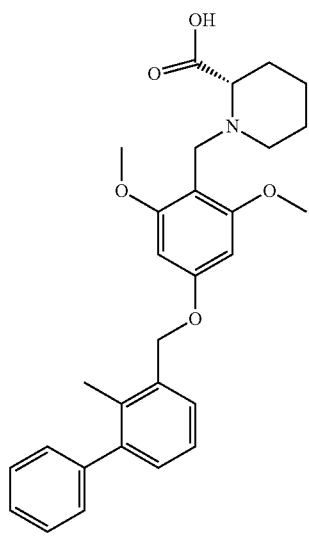 [SMILES: COc1cc(OCc2cccc(-c3ccccc3)c2C)cc(OC)c1CN1CCCC[C@H]1C(=O)O]

It can be seen that the T cell remains active to attack the tumor cell. Astaxanthin manipulates the fatty acids and sterols to address the membrane composition. The astaxanthin reduces intracellular sodium concentrations since an intracellular excess of positively-charged sodium ions reduces the negative interior potential of the inner membrane surface resulting in depolarization of the cell membrane potential. The astaxanthin increases intracellular delivery of magnesium, potassium and calcium. The astaxanthin removes the sialic acid and excessive negative charges from the external surface of the cancer cells (glycocalyx), such as enzymes and electrical treatments, since an excess of negative charges in the glycocalyx can also reduce the membrane potential of cancer cells. The astaxanthin inhibits and alters the electrical charge on PD-L1/PD-L2. It is believed that astaxanthin also plays a role in the inactivation of PD-1 sites on T cells and activation of NK cells. The astaxanthin also corrects intracellular, extracellular and membrane concentrations of the abnormal electrical properties of cancer cells. This includes a reduction of PD-L1 and PD-1 activity. As a result, the cancer cell returns to the normal cellular function or results in cellular apoptosis or cellular lysis.

Astaxanthin's unique molecular structure and lipid solubility allows entire body transport and bioaccumulation throughout our bodies, including neurons and cellular structures within the brain, without any side effects. Once in the cells, unlike other antioxidants, astaxanthin protects the entire cell. Astaxanthin can have one end of its molecule on the outer surface of the cell and the other end in the interior of the cell. The astaxanthin can electrically attach to the PD-L1/PD-L2 sites parallel or perpendicular to the cell membrane. As such, it interferes electrically with the programmed death characteristics of the cell. This full-coverage protection of crossing the phospholipid membrane allows for direct electrical connection between the inside and outside of the cell. This regulates and stabilizes the cellular electrical potential.

Astaxanthin crosses the blood-brain barrier. The astaxanthin also crosses the blood-retinal barrier. The astaxanthin also acts as a hyperactive anti-inflammatory. The astaxanthin can never become a "pro-oxidant". Other antioxidants, under certain conditions, can turn into pro-oxidant and start causing additional oxidation and damage to the body. Astaxanthin acts as an anti-inflammatory that appears to reduce inflammation in the brain. This can have a dramatic effect on amyloidosis diseases, such as Alzheimer's and Parkinson's. In the method of treating the disease, the patient should reduce or eliminate sodium intake by reducing extra-dietary sources of salt. The patient should eliminate all sources of cellular hypoxia, such as smoking and dehydration. Blood oxygen levels, although a good indicator, may not be a good indicator of cellular hypoxia. The degree of cellular oxygenation is determined by the ability of the oxygen to be transported into the cell. This transport is determined by the solubility of oxygen in the interstitial fluid between the capillary and the cell membrane and the concentration gradient across the cell membrane. The astaxanthin can be taken as a checkpoint block on the PD-L1 and PD-L2 sites on the tumor cells. This allows the immune system to attack, lyse the tumor cell wall, or cause apoptosis due to the changes in electrical potential of the cell.

The foregoing disclosure and description of the invention is illustrative and explanatory thereof. Various changes in the details of the present invention can be made is the scope of the present claims without departing from the true spirit of the present invention. The present invention should only be limited by the following claims and their legal equivalents.

I claim:
1. A method of treating a subject afflicted with an inflammatory disease, the method comprising:
   preparing glucosidic astaxanthin by reacting astaxanthin with a monosaccharide at a microwave frequency of between 1 and 100 GHz for at least one second and no more than twenty-five seconds; and
   administering a therapeutic amount of the glucosidic astaxanthin to the subject in need of such treatment.

2. The method of claim 1, the glucosidic astaxanthin having the following chemical structure:

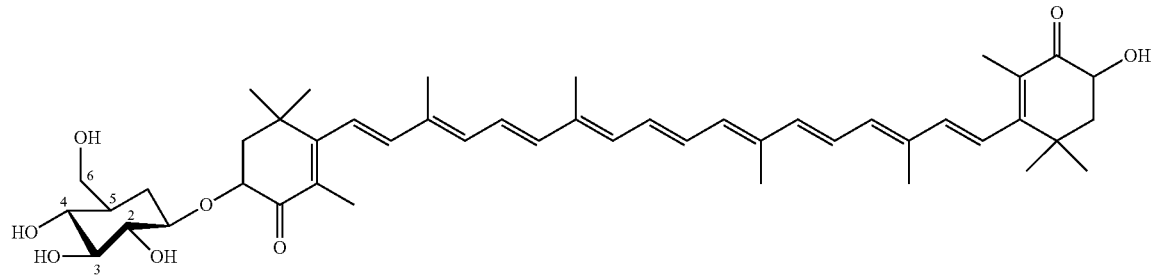

3. The method of claim 1, the step of administering comprising:
adding the glucosidic astaxanthin to a carrier material.

4. The method of claim 3, the carrier material being edible.

5. The method of claim 4, the carrier material being chocolate.

6. The method of claim 3, the carrier material being an oil.

7. The method of claim 1, the therapeutic amount being greater than 0.1 milligrams per kilogram of body weight per day.

8. The method of claim 1, the therapeutic amount being between 24 and 400 milligrams per kilogram of body weight per day.

9. The method of claim 1, the step of administering comprising:
orally consuming the glucosidic astaxanthin.

10. The method of claim 1, the step of administering comprising:
dermally applying the glucosidic astaxanthin onto an area of the skin of the subject where the subject is afflicted with the inflammatory disease.

* * * * *